United States Patent [19]

Reinert

[11] Patent Number: 5,221,287
[45] Date of Patent: Jun. 22, 1993

[54] PROCESS FOR THE PHOTOCHEMICAL AND THERMAL STABILIZATION OF POLYAMIDE FIBRES HAVING AN AFFINITY FOR ACID AND BASIC DYES, AND OF BLENDS OF SAID FIBRES WITH ON ANOTHER AND WITH OTHER FIBRES

[75] Inventor: Gerhard Reinert, Allschwil, Switzerland

[73] Assignee: Ciba-Geigy Corporation, Ardsley, N.Y.

[21] Appl. No.: 543,253

[22] Filed: Jun. 25, 1990

[30] Foreign Application Priority Data

Jun. 27, 1989 [CH] Switzerland ............... 2382/89

[51] Int. Cl.$^5$ .................. D06M 13/35; D06P 1/64
[52] U.S. Cl. ...................... 8/442; 8/115.59; 8/115.66; 8/490; 8/566; 8/568; 544/180; 544/219
[58] Field of Search .............. 8/115.66, 115.7, 442, 8/490, 573, 602, 566, 115.58, 115.59, 568; 252/8.6; 544/219, 180; 546/217

[56] References Cited

U.S. PATENT DOCUMENTS

| | | | |
|---|---|---|---|
| 3,403,183 | 9/1968 | Dobratz | 260/591 |
| 3,640,928 | 2/1972 | Morzema | 524/102 |
| 3,993,655 | 1/1976 | Rasberger | 260/293 |
| 4,127,586 | 11/1978 | Rody | 260/308 |
| 4,166,803 | 9/1979 | Jrick | 252/402 |
| 4,511,596 | 4/1985 | Berner | 427/44 |
| 4,537,923 | 8/1985 | Slongo | 524/100 |
| 4,775,386 | 10/1988 | Reinert et al. | 8/442 |
| 4,780,494 | 10/1988 | Hess | 524/99 |
| 4,874,391 | 10/1989 | Reinert | 8/442 |
| 5,160,346 | 11/1992 | Fujo et al. | 8/442 |

FOREIGN PATENT DOCUMENTS

| | | |
|---|---|---|
| 0097616 | 1/1984 | European Pat. Off. . |
| 0243319 | 10/1987 | European Pat. Off. . |
| 0255481 | 2/1988 | European Pat. Off. . |
| 1929928 | 1/1970 | Fed. Rep. of Germany . |
| 2204659 | 8/1972 | Fed. Rep. of Germany . |
| 2453146 | 5/1976 | Fed. Rep. of Germany . |
| 2253742 | 12/1973 | France . |
| 2157294 | 10/1985 | United Kingdom . |

OTHER PUBLICATIONS

Synthesis 11, 901 (1984) p. 901.
Houben-Weyl, Methoden der Organischen Chemie X (1), 1280 (1971).
Dexter, Kirk-Othmer 23, 615-627.
A. F. Strobel, Am dyestuff Rep. 50 583-588 (1961) p. 19.
A. F. Strobel 51, 99-104 (1962) Am. Dyestuff Rep.
F. Gugumus, Lichtschutzmittel fur thermoplastics Kunstoffe, Taschenbuch der Kunststoffadditive 101-198.
H. Brunetti 55, (1972) p. 21 Helv. Chim. Acta.

*Primary Examiner*—Anthony McFarland
*Attorney, Agent, or Firm*—George R. Dohmann; Marla J. Mathias

[57] ABSTRACT

The invention describes a process for the photochemical and thermal stabilization of polyamide fibres having an affinity for acid and basic dyes, and of blends of said fibres with one another and with other fibres, a composition for carrying out the process and the fibre materials treated therewith.

19 Claims, No Drawings

PROCESS FOR THE PHOTOCHEMICAL AND THERMAL STABILIZATION OF POLYAMIDE FIBRES HAVING AN AFFINITY FOR ACID AND BASIC DYES, AND OF BLENDS OF SAID FIBRES WITH ON ANOTHER AND WITH OTHER FIBRES

The present invention relates to a process for the photochemical and thermal stabilization of polyamide fibres having an affinity for acid and basic dyes, and of blends of said fibres with one another and with other fibres, to a composition for carrying out the process and to the fibre materials treated therewith.

Undyed and textile-finished polyamide fibre material and polyamide having an affinity for basic dyes, as well as blends thereof with one another and with other fibres, are damaged, as are the dyeings of these substrates, under the action of light and especially when there is simultaneous thermal radiation. Thus the photochemical stability of these fibres dyed with selected dyes, for example in motor vehicle trim, is not adequate.

It is known from European patent application 0 255 481 to improve the light fastness properties of polyamide fibre blends by treatment with a mixture of copper complex dyes, light stabilizers and antioxidants.

It has now been found that a good light and heat stabilization is achieved by treating these fibres with light stabilizers from the class of the sterically hindered amines, in the absence of metal-containing compounds. These substances can preferably be used in the dyebath.

These light stabilizers are preferably of interest in cases where it is undesirable to use metal-containing compounds, e.g. for modified PA fibres and in particular for blends or structures of polyamide fibres with polypropylene fibres or the various polyurethane fibres.

The present invention thus relates to a process for the photochemical and thermal stabilization of polyamide fibres having an affinity for acid and basic dyes, and of blends of said fibres with one another and with other fibres, which comprises treating the fibre material with an aqueous liquor containing a light stabilizer from the class of the sterically hindered amines.

A light stabilizer which can be used according to the invention is a sterically hindered amine whose molecule contains at least one group of formula I

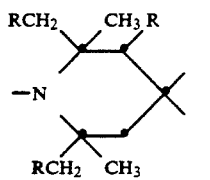
(I)

wherein R is hydrogen or methyl.

Such light stabilizers can be low-molecular (MW <700) or higher-molecular (oligomers, polymers). Preferably, these groups carry one or two polar substituents in the 4-position or a polar spiro ring system is bonded to the 4-position.

Especially preferred light stabilizers are
a) Sterically hindered amines of formula II

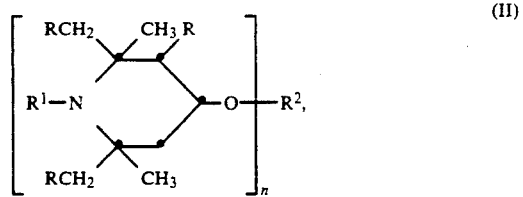
(II)

wherein n is a number from 1 to 4, preferably 1 or 2, R is hydrogen or methyl, $R^1$ is hydrogen, hydroxyl, $C_1$–$C_{12}$ alkyl, $C_3$–$C_8$ alkenyl, $C_3$–$C_8$ alkynyl, $C_7$–$C_{12}$ aralkyl, $C_1$–$C_8$ alkanoyl, $C_3$–$C_5$ alkenoyl, glycidyl, —O—$C_1$–$C_{12}$ alkyl, —O—$C_1$–$C_8$ alkanoyl or a group —$CH_2CH(OH)$—Z, wherein Z is hydrogen, methyl or phenyl, $R^1$ preferably being hydrogen, $C_1$–$C_4$ alkyl, allyl, benzyl, acetyl or acryloyl, and $R^2$ when n is 1 is hydrogen, $C_1$–$C_{18}$ alkyl which may or may not be interrupted by one or more oxygen atoms, cyanoethyl, benzyl, glycidyl, a monovalent radical of an aliphatic, cycloaliphatic, araliphatic, unsaturated or aromatic carboxylic acid, carbamic acid or phosphorus-containing acid, or a monovalent silyl radical, preferably a radical of an aliphatic carboxylic acid having 2 to 18 C atoms, of a cycloaliphatic carboxylic acid having 7 to 15 C atoms, of an $\alpha,\beta$- unsaturated carboxylic acid having 3 to 5 C atoms or of an aromatic carboxylic acid having 7 to 15 C atoms, $R^2$ when n is 2 is $C_1$–$C_{12}$ alkylene, $C_4$–$C_{12}$ alkenylene, xylylene, a divalent radical of an aliphatic, cycloaliphatic, araliphatic or aromatic dicarboxylic acid, dicarbamic acid or phosphorus-containing acid, or a divalent silyl radical, preferably a radical of an aliphatic dicarboxylic acid having 2 to 36 C atoms, of a cycloaliphatic or aromatic dicarboxylic acid having 8-14 C atoms or of an aliphatic, cycloaliphatic or aromatic dicarbamic acid having 8-14 C atoms, $R^2$ when n is 3 is a trivalent radical of an aliphatic, cycloaliphatic or aromatic tricarboxylic acid, aromatic tricarbamic acid or phosphorus-containing acid, or a trivalent silyl radical, and $R^2$ when n is 4 is a tetravalent radical of an aliphatic, cycloaliphatic or aromatic tetracarboxylic acid.

Any $C_1$–$C_{12}$ alkyl substituents are e.g. methyl, ethyl, n-propyl, n-butyl, sec-butyl, tert-butyl, n-hexyl, n-octyl, 2-ethylhexyl, n-nonyl, n-decyl, n-undecyl or n-dodecyl.

$R^1$ or $R^2$ as $C_1$–$C_{18}$ alkyl can be e.g. the groups mentioned above and also, for example, n-tridecyl, n-tetradecyl, n-hexadecyl or n-octadecyl.

$R^1$ as $C_3$–$C_8$ alkenyl can be e.g. prop-1-enyl, allyl, methallyl, but-2-enyl, pent-2-enyl, hex-2-enyl, oct-2-enyl or 4-tert-butylbut-2-enyl.

$R^1$ as $C_3$–$C_8$ alkynyl is preferably propargyl.

$R^1$ as $C_7$–$C_{12}$ aralkyl is especially phenethyl and in particular benzyl.

$R^1$ as $C_1$–$C_8$ alkanoyl is, for example, formyl, propionyl, butyryl, octanoyl or, preferably, acetyl and $R^1$ as $C_3$–$C_5$ alkanoyl is especially acryloyl.

$R^2$ as a monovalent radical of a carboxylic acid is, for example, an acetic acid, caproic acid, stearic acid, acrylic acid, methacrylic acid, benzoic acid or $\beta$-(3,5-di-tert-butyl-4-hydroxyphenyl)propionic acid radical.

$R^2$ as a divalent radical of a dicarboxylic acid is, for example, a malonic acid, succinic acid, glutaric acid, adipic acid, suberic acid, sebacic acid, maleic acid, phthalic acid, dibutylmalonic acid, dibenzylmalonic acid, butyl(3,5-di-tert-butyl-4-hydroxybenzyl)malonic acid or bicycloheptenedicarboxylic acid radical.

$R^2$ as a trivalent radical of a tricarboxylic acid is e.g. a trimellitic acid or nitrilotriacetic acid radical.

$R^2$ as a tetravalent radical of a tetracarboxylic acid is e.g. the tetravalent radical of butane-1,2,3,4-tetracarboxylic acid or of pyromellitic acid.

$R^2$ as a divalent radical of a dicarbamic acid is, for example, a hexamethylenedicarbamic acid or 2,4-toluylenedicarbamic acid radical.

The following compounds are examples of polyalkylpiperidine compounds of this class:
1) 4-hydroxy-2,2,6,6-tetramethylpiperidine
2) 1-allyl-4-hydroxy-2,2,6,6-tetramethylpiperidine
3) 1-benzyl-4-hydroxy-2,2,6,6-tetramethylpiperidine
4) 1-(4-tert-butylbut-2-enyl)-4-hydroxy-2,2,6,6-tetramethylpiperidine
5) 4-stearoyloxy-2,2,6,6-tetramethylpiperidine
6) 1-ethyl-4-salicyloyloxy-2,2,6,6-tetramethylpiperidine
7) 4-methacryloyloxy-1,2,2,6,6-pentamethylpiperidine
8) 1,2,2,6,6-pentamethylpiperidin-4-yl β-(3,5-di-tert-butyl-4-hydroxyphenyl)propionate
9) di(1-benzyl-2,2,6,6-tetramethylpiperidin-4-yl) maleate
10) di(2,2,6,6-tetramethylpiperidin-4-yl) succinate
11) di(2,2,6,6-tetramethylpiperidin-4-yl) glutarate
12) di(2,2,6,6-tetramethylpiperidin-4-yl) adipate
13) di(2,2,6,6-tetramethylpiperidin-4-yl) sebacate
14) di(1,2,2,6,6-pentamethylpiperidin-4-yl) sebacate
15) di(1,2,3,6-tetramethyl-2,6-diethylpiperidin-4-yl) sebacate
16) di(1-allyl-2,2,6,6-tetramethylpiperidin-4-yl) phthalate
17) 1-propargyl-4-β-cyanoethoxy-2,2,6,6-tetramethylpiperidine
18) 1-acetyl-2,2,6,6-tetramethylpiperidin-4-yl acetate
19) tri(2,2,6,6-tetramethylpiperidin-4-yl) trimellitate
20) 1-acryloyl-4-benzyloxy-2,2,6,6-tetramethylpiperidine
21) di(2,2,6,6-tetramethylpiperidin-4-yl) diethylmalonate
22) di(1,2,2,6,6-pentamethylpiperidin-4-yl) dibutylmalonate
23) di(1,2,2,6,6-pentamethylpiperidin-4-yl) butyl(3,5-di-tert-butyl-4-hydroxybenzyl)malonate
24) di(1,2,2,6,6-pentamethylpiperidin-4-yl) dibenzylmalonate
25) di(1,2,3,6-tetramethyl-2,6-diethylpiperdin-4yl) -yl) dibenzylmalonate
26) hexane-1',6'-bis(4-carbamoyloxy-1-n-butyl-2,2,6,6-tetramethylpiperidine)
27) toluene-2',4'-bis(4-carbamoyloxy-1-n-propyl-2,2,6,6-tetramethylpiperidine)
28) dimethyl-bis(2,2,6,6-tetramethylpiperidin-4-oxy)silane
29) phenyl-tris(2,2,6,6-tetramethylpiperidin-4-oxy)silane
30) tris(1-propyl-2,2,6,6-tetramethylpiperidin-4-yl) phosphite
31) tris(1-propyl-2,2,6,6-tetramethylpiperidin-4-yl) phosphate
32) phenyl[bis(1,2,2,6,6-pentamethylpiperidin-4-yl)] phosphonate
33) 4-hydroxy-1,2,2,6,6-pentamethylpiperidine
34) 4-hydroxy-N-hydroxyethyl-2,2,6,6-tetramethylpiperidine
35) 4-hydroxy-N-(2-hydroxypropyl)-2,2,6,6-tetramethylpiperidine
36) 1-glycidyl-4-hydroxy-2,2,6,6-tetramethylpiperidine
b) Compounds of formula (III)

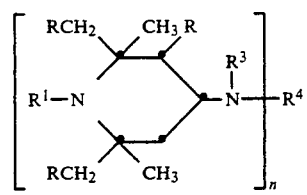

(III)

wherein n is the number 1 or 2, R and $R^1$ are as defined under a), $R^3$ is hydrogen, $C_1$–$C_{12}$ alkyl, $C_2$–$C_5$ hydroxyalkyl, $C_5$–$C_7$ cycloalkyl, $C_7$–$C_8$ aralkyl, $C_2$–$C_{18}$ alkanoyl, $C_3$–$C_5$ alkenoyl or benzoyl and $R^4$ when n is 1 is hydrogen, $C_1$–$C_{18}$ alkyl, $C_3$–$C_8$ alkenyl, $C_5$–$C_7$ cycloalkyl, $C_1$–$C_4$ alkyl substituted by a hydroxyl, cyano, alkoxycarbonyl or carbamide group, glycidyl or a group of the formula —$CH_2$—CH(OH)—Z or of the formula —CONH—Z, wherein Z is hydrogen, methyl or phenyl, $R^4$ when n is 2 is $C_2$–$C_{12}$ alkylene, $C_6$–$C_{12}$ arylene, xylylene, a group —$CH_2$—CH(OH)—$CH_2$— or a group —$CH_2$—CH(OH)—$CH_2$—O—D—O—, wherein D is $C_2$–$C_{10}$ alkylene, $C_6$–$C_{15}$ arylene or $C_6$–$C_{12}$ cycloalkylene, or, with the proviso that $R^3$ is not alkanoyl, alkenoyl or benzoyl, $R^4$ can also be a divalent radical of an aliphatic, cycloaliphatic or aromatic dicarboxylic acid or dicarbamic acid, or the group —CO—, or $R^3$ and $R^4$ when n is 1 can together be the divalent radical of an aliphatic, cycloaliphatic or aromatic 1,2- or 1,3-dicarboxylic acid.

Any $C_1$–$C_{12}$ or $C_1$–$C_{18}$ alkyl substituents are as defined under a).

Any $C_5$–$C_7$ cycloalkyl substituents are especially cyclohexyl.

$R^3$ as $C_7$–$C_8$ aralkyl is especially phenylethyl or in particular benzyl.

$R^3$ as $C_2$–$C_5$ hydroxyalkyl is especially 2-hydroxyethyl or 2-hydroxypropyl.

$R^3$ as $C_2$–$C_{18}$ alkanoyl is, for example, propionyl, butyryl, octanoyl, dodecanoyl, hexadecanoyl, octadecanoyl or, preferably, acetyl and $R^3$ as $C_3$–$C_5$ alkenoyl is especially acryloyl.

$R^4$ as $C_2$–$C_8$ alkenyl is e.g. allyl, methallyl, but-2-enyl, pent-2-enyl, hex-2-enyl or oct-2-enyl.

$R^4$ as $C_1$–$C_4$ alkyl substituted by a hydroxyl, cyano, alkoxycarbonyl or carbamide group can be e.g. 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

Any $C_2$–$C_{12}$ alkylene substituents are e.g. ethylene, propylene, 2,2-dimethylpropylene, tetramethylene, hexamethylene, octamethylene, decamethylene or dodecamethylene.

Any $C_6$–$C_{15}$ arylene substituents are e.g. o-, m- or p-phenylene, 1,4-naphthylene or 4,4'-diphenylene.

D as $C_6$–$C_{12}$ cycloalkylene is especially cyclohexylene.

The following compounds are examples of polyalkylpiperidine compounds of this class:
37) N,N'-bis(2,2,6,6-tetramethylpiperidin-4-yl)hexamethylene-1,6-diamine
38) N,N'-bis(2,2,6,6-tetramethylpiperidin-4-yl)hexamethylene-1,6-diacetamide
39) 1-acetyl-4-(N-cyclohexylacetamido)-2,2,6,6-tetramethylpiperidine
40) 4-benzoylamino-2,2,6,6-tetramethylpiperidine
41) N,N'-bis(2,2,6,6-tetramethylpiperidin-4-yl)-N,N'-dibutyladipamide 42) N,N'-bis(2,2,6,6-tetramethylpiperidin-4-yl)-N,N'-dicyclohexyl-2-hydroxypropylene-1,3-diamine
43) N,N'-bis(2,2,6,6-tetramethylpiperidin-4-yl)-p-xylylenediamine
44) N,N'-bis(2,2,6,6-tetramethylpiperidin-4-yl)succindiamide
45) di(2,2,6,6-tetramethylpiperidin-4-yl) N-(2,2,6,6-tetramethylpiperidin-4-yl)-β-aminodipropionate
46) the compound of the formula

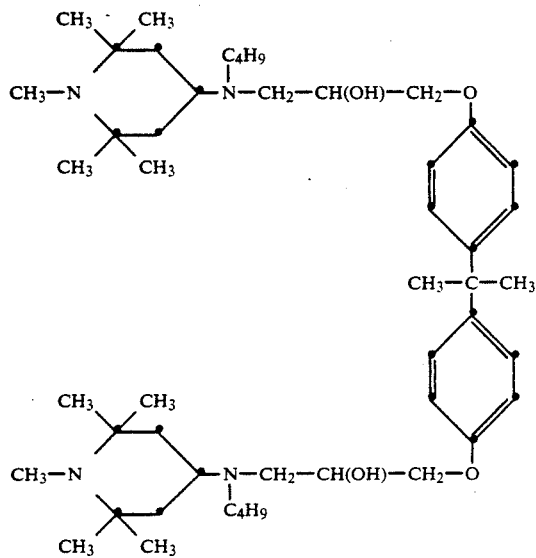

47) 4-(bis-2-hydroxyethylamino)-1,2,2,6,6-pentamethylpiperidine
48) 4-(3-methyl-4-hydroxy-5-tert-butylbenzamido)-2,2,6,6-tetramethylpiperidine
49) 4-methacrylamido-1,2,2,6,6-pentamethylpiperidine c) Compounds of formula IV

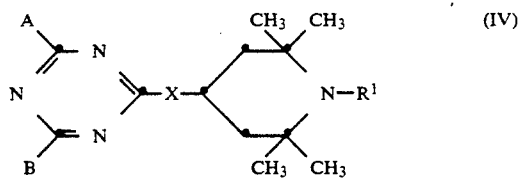
(IV)

wherein $R^1$ is hydrogen, oxyl oxygen, $C_1-C_{12}$ alkyl, $C_3-C_7$ alkenyl, $C_7-C_{11}$ phenylalkyl, cyanomethyl, $C_2-C_{18}$ alkanoyl, $C_3-C_{18}$ alkenoyl, a group —CON($R^2$)($R^3$) or a group —CH$_2$—CH($R^4$)—OH, wherein $R^2$ is $C_1-C_{12}$ alkyl, allyl, cyclohexyl, benzyl, phenyl or $C_7-C_{12}$ alkylphenyl and $R^3$ is hydrogen, $C_1-C_{12}$ alkyl, allyl or benzyl, or $R^2$ and $R^3$ form a 5- or 6-membered heterocyclic ring together with the N atom to which they are bonded, and $R^4$ is hydrogen, $C_1-C_{12}$ alkyl, phenyl, $C_2-C_{13}$ alkoxymethyl or phenoxymethyl, X is a divalent group of the formula —O—, —N($R^5$)—, —NH—(CH$_2$)$_2$—O—, —NH—(CH$_2$)$_3$—O— or —N($R^5$)—$R^7$—N($R^6$)—, wherein $R^5$ is hydrogen, $C_1-C_{12}$ alkyl, $C_3-C_7$ alkenyl, cyclohexyl, $C_3-C_{12}$ alkoxyalkyl, $C_5-C_{12}$ alkenoxyalkyl, $C_4-C_{12}$ dialkylaminoalkyl, a group —CH$_2$—CH($R^4$)—OH, benzyl or a group of the formula

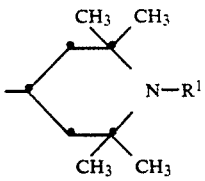

or of the formula

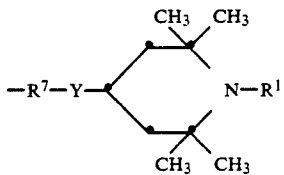

$R^6$ is hydrogen, $C_1-C_{12}$ alkyl, $C_3-C_7$ alkenyl, cyclohexyl, a group —CH$_2$—CH($R^4$)—OH or a group of the formula

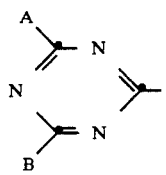

$R^7$ is $C_2-C_{12}$ alkylene which can be interrupted by 1, 2 or 3 of the groups —O— or —N($R^6$)—, $C_6-C_{14}$ cycloalkylene or cycloalkylenedialkylene and Y is a divalent group of the formula —O— or —N($R^6$)—, and A and B independently of the other are a group of the formula $R^8$O— or ($R^9$)($R^{10}$)N—, wherein $R^8$ is $C_1-C_{12}$ alkyl, $C_3-C_7$ alkenyl, cyclohexyl, benzyl, phenyl or $C_7-C_{12}$ alkylphenyl, $R^9$ is $C_1-C_{12}$ alkyl, $C_3-C_7$ alkenyl, $C_5-C_8$ cycloalkyl, $C_3-C_{12}$ alkoxyalkyl, $C_5-C_{12}$ alkenoxyalkyl, a group —CH$_2$—CH($R^4$)—OH, phenyl, $C_7-C_{12}$ alkylphenyl or $C_7-C_{11}$ phenylalkyl and $R^{10}$ is hydrogen, $C_1-C_{12}$ alkyl, $C_3-C_7$ alkenyl, $C_5-C_8$ cycloalkyl, $C_3-C_{12}$ alkoxyalkyl, $C_5-C_{12}$ alkenoxyalkyl, a group —CH$_2$—CH($R^4$)—OH or $C_7-C_{11}$ phenylalkyl, or $R^9$ and $R^{10}$ form a 5- or 6-membered heterocyclic ring together with the N atom to which they are bonded.

The substituents $R^1$, $R^2$, $R^4$, $R^5$, $R^6$, $R^8$, $R^9$ and $R^{10}$ as alkyl can be unbranched or branched alkyl, preferably unbranched alkyl. Examples of such alkyl groups are methyl, ethyl, propyl, butyl, sec-butyl, n-hexyl, n-octyl, 2-ethylhexyl, n-decyl or n-dodecyl.

$R^1$, $R^5$, $R^6$, and $R^8$ and $R^9$ as alkenyl can be unbranched or branched alkenyl, e.g. allyl, methallyl, but-2-en-1-yl, 2-methylbut-2-en-1-yl or hex-2-en-1yl, allyl being preferred.

$R^9$ as cycloalkyl can be e.g. cyclopentyl, cyclohexyl, 4-methylcyclohexyl, cycloheptyl or cyclooctyl, cyclohexyl being preferred.

$R^1$, $R^9$ and $R^{10}$ as phenylalkyl can be e.g. benzyl, 1-phenylethyl, 2-phenylethyl, 3-phenylpropyl or 3-phenylbutyl, benzyl being preferred.

$R^2$, $R^8$ and $R^9$ as alkylphenyl can be e.g. 4-tolyl, 2-tolyl, 3,5-dimethylphenyl, 4-ethylphenyl or 4-isopropylphenyl, 4-tolyl being preferred.

$R^1$ as alkanoyl can be e.g. acetyl, propionyl, butyryl, hexanoyl (capronyl), 2-ethylhexanoyl, n-octanoyl (capryloyl), n-decanoyl (caprinoyl), n-dodecanoyl (lauroyl), n-hexadecanoyl (palmitoyl) or n-octadecanoyl (stearoyl). $R^1$ as alkenoyl can be e.g. acryloyl, methacryloyl, crotonyl, vinylacetyl or oleyl.

$R^4$ as alkoxymethyl can be e.g. methoxymethyl, ethoxymethyl, butoxymethyl, hexyloxymethyl, octyloxymethyl or dodecyloxymethyl.

$R^5$ and $R^9$ as alkoxyalkyl can be e.g. 2-methoxyethyl, 2-ethoxyethyl, 2-isopropoxyethyl, 2-butoxyethyl, 2-methoxypropyl, 4-methoxybutyl, 3-butoxypropyl or 2-octyloxyethyl. $R^5$ and $R^9$ as alkenoxyalkyl can be e.g. 2-allyloxyethyl, 2-methallyloxypropyl or 3-allyloxypropyl.

$R^5$ as dialkylaminoalkyl can be especially dialkylaminopropyl, e.g. 3-dimethylaminopropyl, 3-diethylaminopropyl or 3-diisopropylaminopropyl.

$R^7$ as alkylene or alkylene interrupted by —O— or —N($R^6$)— can be e.g. 1,2-ethylene, 1,3-propylene, 1,4-butylene, 1,6-hexylene, 1,8-octylene, 2,4-dimethyl-1,6-hexylene, 1,12-dodecylene, 4-oxa-1,7-heptylene, 4-methylaza-1,7-heptylene or 4,8-diaza-1,11-undecylene.

$R^7$ as cycloalkylene or cycloalkylenedialkylene can be e.g. 1,4-cyclohexylene, 1,5-cyclooctylene, 1,4-dimethylenecyclohexane or 3,3-dimethyl-5-methylenecyclohexyl.

$R^2$ and $R^3$, and $R^9$ and $R^{10}$, together with the N atom to which they are bonded, can form a heterocyclic ring such as a pyrrolidine, piperidine, morpholine or 4-methylpiperazine ring.

Preferred compounds of formula IV are:

1a) Compounds of formula IV wherein at least two of the groups $R^1$, $R^2$, $R^3$, $R^5$, $R^6$, $R^8$, $R^9$ or $R^{10}$ are alkenyl or alkenoyl.

1b) Compounds of formula IV wherein the substituent A is a group $R^{15}O$— or $(R^{15})(R^{10})N$— and $R^{15}$ is $C_3$–$C_7$ alkenyl.

1c) Compounds of formula IV wherein A and B are a group of the formula $R^{15}O$— or $(R^{15})(R^{10})N$— and $R^{15}$ is allyl.

1d) Compounds of formula IV wherein the substituents A and B are a group $R^8O$— or $(R^9)(R^{10})N$— wherein $R^8$ and $R^9$ are allyl, and X is a group —N($R^5$)— wherein $R^5$ is a group of the formula

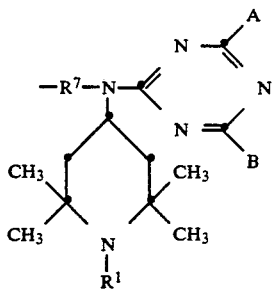

and A, B, $R^1$ and $R^7$ are as defined above.

Examples of compounds of formula (IV) are:

2,4-bis[N-(2,2,6,6-tetramethylpiperid-4-yl)butylamino]-6-allylamino-1,3,5-triazine, m.p. 101°–103° C., N,N'-bis[2,4-bis(diallylamino)-1,3,5-triazin-6-yl]-N,N'-bis(2,2,6,6-tetramethylpiperid-4-yl)hexamethylenediamine, m.p. 124°–125° C., 2,4-bis(diallylamino)-6-[N-(2,2,6,6-tetramethylpiperid-4-yl)butylamino]-1,3,5-triazine, viscous oil, b.p. 230° C./0.1 Pa, N,N'-bis[2,4-di(allyloxy)-1,3,5-triazin-6-yl]-N,N'-bis(2,2,6,6-tetramethylpiperid-4-yl)hexamethylenediamine, m.p. 112°–113° C., and N,N'-bis[2,4-di(allylamino)-1,3,5-triazin-6-yl]-N,N'-bis(2,2,6,6-tetramethylpiperid-4-yl)hexamethylenediamine, m.p. 162°–163° C.

The most preferred compounds of formula (IV) are those in which A and B are a group of the formula $R^{15}O$— or $(R^{15})(R^{10})N$— and $R^{15}$ is allyl.

The compounds of formulae (II) and (III) are known e.g. from U.S. Pats. Nos. 3,840,494, 3,640,928 and 3,993,655 and can be prepared by the processes described therein.

The compounds of formula (IV) can be prepared analogously to the process of U.S. Pat. No. 3,925,376 by reacting cyanuric chloride stepwise with the components AH and BH and with a 4-hydroxy- or 4-amino-2,2,6,6-tetramethylpiperidine. The introduction of the substituent $R^1$ on to the piperidine nitrogen can take place before or after the reaction with the halogenotriazine.

The compounds of formulae (I) to (IV) are conveniently used as emulsions or fine dispersions obtained by grinding or in the presence of non-ionic or anionic dispersants.

Suitable non-ionic dispersants are alkylene oxide reaction products of alcohols or alkylphenols, e.g. alkylene oxide reaction products of aliphatic alcohols having 4 to 22 carbon atoms, which contain up to 80 mol of ethylene oxide and/or propylene oxide added on. The alcohols can preferably contain 4 to 18 carbon atoms, they can be saturated, branched or linear and they can be used on their own or in a mixture. Branched-chain alcohols are preferred.

It is possible to use naturally occurring alcohols such as myristyl alcohol, cetyl alcohol, stearyl alcohol, oleyl alcohol, arachidyl alcohol or behenyl alcohol, or synthetic alcohols such as, in particular, butanol, 2-ethylhexanol, amyl alcohol or n-hexanol, or also triethylhexanol or trimethylnonyl alcohol, or mixtures of higher fatty alcohols, these being linear primary alcohols.

Preferred ethylene oxide/alcohol reaction products can be represented e.g. by the formula $$R_3O(CH_2CH_2O)_sH,$$

wherein $R_3$ is a saturated or unsaturated hydrocarbon radical, preferably an alkyl or alkenyl radical having 8 to 18 carbon atoms, and s is an integer from 1 to 80, preferably from 1 to 30.

Other suitable non-ionic dispersants are reaction products of ethylene oxide and/or 1,2-propylene oxide and alkylphenols having 4 to 12 carbon atoms in the alkyl moiety, it being possible for the phenol to contain one or more alkyl substituents. These compounds preferably have the formula

wherein R is hydrogen or at most one of the two radicals R is methyl, p is a number from 4 to 12, preferably 8 to 9, and t is a number from 1 to 60, especially from 1 to 20 and preferably 1 to 6.

If desired, these ethylene oxide/1,2-propylene oxide adducts of alcohols or alkylphenols can contain even smaller proportions of block polymers of said alkylene oxides.

Other reaction products which are suitable as nonionic dispersants are polyoxyethylene derivatives of the fatty acid esters of sorbitan ethers with 4 mol of polyethylene glycol, e.g. the laurate, palmitate, stearate, tristearate, oleate and trioleate of said ethers, such as the Tween brands from Atlas Chemicals Division. It is preferred to use the tristearate of the sorbitan ether with 4 mol of polyethylene glycol, of the formula $$H(CH_2CH_2)_{65}OH.$$

Suitable anionic dispersants are esterified alkylene oxide adducts, e.g. addition products, containing acidic ester groups of inorganic or organic acids, of alkylene oxides, especially ethylene oxide and/or propylene oxide, and aliphatic organic hydroxyl, carboxyl or also, if appropriate, amino or amido compounds having a total of at least 8 carbon atoms, or mixtures of these compounds. These acidic esters can be in the form of free acids or in the form of salts, e.g. alkali metal, alkaline earth metal, ammonium or amine salts.

These anionic dispersants are prepared according to known methods by adding at least 1 mol, preferably more than 1 mol, e.g. 2 to 60 mol, of ethylene oxide, or of ethylene oxide and propylene oxide alternately in any order, on to said organic compounds, then etherifying or esterifying the addition products and, if desired, converting the ethers or esters into their salts. Examples of suitable starting materials are higher fatty alcohols, i.e. alkanols or alkenols having 8 to 22 carbon atoms, alicyclic alcohols, phenylphenols or alkylphenols having one or more alkyl substituents which contains or which together contain at least 10 carbon atoms, or fatty acids having 8 to 22 carbon atoms.

Especially suitable anionic dispersants have the formula $$R_1-A-(CH_2CHO)_n-Q, \quad (V)$$
$$\qquad\qquad\quad |$$
$$\qquad\qquad\quad R_2$$

wherein $R_1$ is an aliphatic hydrocarbon radical having 8 to 22 carbon atoms or a cycloaliphatic, aromatic or aliphatic-aromatic hydrocarbon radical having 10 to 22 carbon atoms, $R_2$ is hydrogen or methyl, A is —O— or $$-C-O,$$
$$\parallel$$
$$O$$

Q is the acid radical of an inorganic oxygen-containing acid, the acid radical of a polybasic carboxylic acid or a carboxyalkyl radical and n is a number from 1 to 50.

The radical $R_1-A-$ in the compounds of formula (V) is derived e.g. from higher alcohols such as decyl, lauryl, tridecyl, myristyl, cetyl, stearyl, oleyl, arachidyl or behenyl alcohol, from alicyclic alcohols such as hydroabietyl alcohol, from fatty acids such as caprylic, capric, lauric, myristic, palmitic, stearic, arachidic or behenic acid, coconut fatty acid ($C_8-C_{18}$) or decenoic, dodecenoic, tetradecenoic, hexadecenoic, oleic, linoleic, linolenic, eicosenoic, docosenoic or clupanodonic acid, from alkylphenols such as butylphenol, hexylphenol, n-octylphenol, n-nonylphenol, p-tert-octylphenol, p-tert-nonylphenol, decylphenol, dodecylphenol, tetradecylphenol or hexadecylphenol, or from arylphenols such as o- or p-phenylphenols. Radicals having 10 to 18 carbon atoms are preferred and those derived from the alkylphenols are especially preferred.

The acid radical Q is generally the acid radical of a polybasic and especially low-molecular monocarboxylic or dicarboxylic acid, e.g. of maleic acid, malonic acid, succinic acid or sulfosuccinic acid, or is a carboxyalkyl radical, especially a carboxymethyl radical (derived from chloroacetic acid in particular), and is bonded to the radical $R_1-A-(CH_2CHR_1O)_m-$ via an ether or ester bridge. In particular, however, Q is derived from inorganic polybasic acids such as orthophosphoric acid and sulfuric acid. The acid radical X is preferably in the form of a salt, e.g. in the form of an alkali metal, ammonium or amine salt.

Examples of such salts are sodium, potassium, ammonium, trimethylamine, ethanolamine, diethanolamine or triethanolamine salts. The alkylene oxide units $-CH_2CHR_2O-$ of formula (V) are generally ethylene oxide and 1,2-propylene oxide units, the latter preferably being present in a mixture with ethylene oxide units in the compounds of formula (V).

Especially preferred anionic compounds are those of the formula $$R_3O(CH_2CH_2O)_n-X,$$

wherein $R_3$ is a saturated or unsaturated hydrocarbon radical having 8 to 22 carbon atoms, o-phenylphenyl or alkylphenyl having 4 to 12 carbon atoms in the alkyl moiety, and X and n are as defined.

Of the compounds derived from alkylphenol/ethylene oxide adducts, those of the formulae

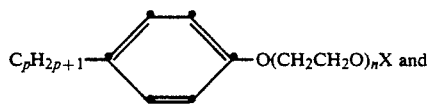

and

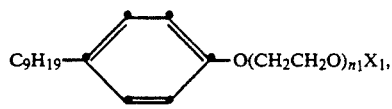

wherein p is a number from 4 to 12, n is an integer from 1 to 20, $n_1$ is an integer from 1 to 10, $X_1$ is a sulfuric acid or phosphoric acid radical, if desired in the form of a salt, and X is as defined, are also especially preferred.

Examples of other suitable dispersants are the known ligninsulfonates, condensation products of naphthalenesulfonic acid and/or naphtholsulfonic or naphthylaminosulfonic acids with formaldehyde, and condensation products of phenolsulfonic acids and/or phenols with formaldehyde and urea.

Other especially suitable dispersants are sulfonated condensation products which have been obtained by reacting an aromatic compound containing at least two replaceable ring hydrogen atoms, in any order, with a compound of the formula

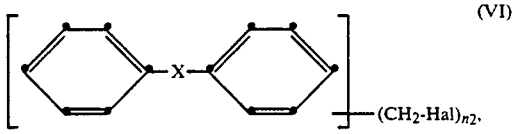

(VI)

wherein X is a direct bond or oxygen, Hal is chloro or bromo and $n_2$ is 1 to 4, and then sulfonating the reaction product.

These sulfonated condensation products preferably have the formula

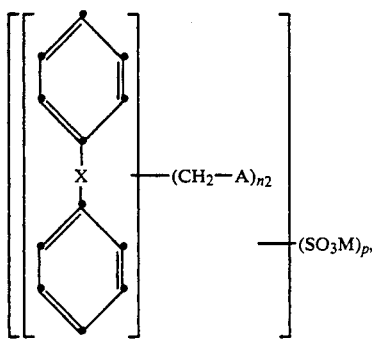

in which X is a direct bond or oxygen, A is the radical of an aromatic compound which is bonded to the methylene group by means of a ring carbon atom, M is hydrogen or a cation, e.g. an alkali metal, an alkaline earth metal or an ammonium group, and $n_2$ and p are each a number from 1 to 4. $n_2$ and p are preferably 1 or 2, but they can also each be any fraction from 1 to 4, e.g. 1.4, 1.8, 2.1 or 3.2.

Aromatic compounds containing at least two replaceable hydrogen atoms can be mononuclear or polynuclear hydrocarbons, especially dinuclear hydrocarbons, which may be substituted. Examples of suitable substituents are hydroxyl groups, alkyl groups having 1 to 4 carbon atoms, alkoxy groups having 1 to 4 carbon atoms or halogeno, e.g. chloro. The preferred compounds are naphthalene compounds which can be substituted by hydroxyl, chloro or methyl. The following are examples of mononuclear and polynuclear aromatic compounds: alkylbenzenes such as toluene, xylenes, isopropylbenzene, isobutylbenzene or tert-butylbenzene; phenol; chlorophenols; alkylphenols such as methylphenol, dimethylphenol, isopropylphenol or tert-butylphenol; hydroxybiphenyls; alkoxybenzenes such as anisoles, phenetoles or butoxybenzene; diphenylalkanes; hydroxydiphenylalkanes; tetrahydronaphthalene; naphthalene; α- and β-naphthol; alkylnaphthalenes such as α- and β- methylnaphthalene; and acenaphthene, anthracene, perylene, pyrene, dihydrophenanthrene or phenanthrene. Naphthalene, which may also already be sulfonated, is especially suitable. Of course, it is also possible to use mixture of these mononuclear and polynuclear aromatic compounds as starting materials.

The compounds of formula (VI) which are also required as starting materials are prepared e.g. by reacting biphenyl or diphenyl ether with formaldehyde and a hydrogen halide such as hydrogen bromide or, preferably, hydrogen chloride, according to the methods described in U.S. Pat. No. 3,004,072 or Italian patent 600 214.

Preferred starting materials of formula (VI) are chloromethylbiphenyl and chloromethyldiphenyl ether. These compounds are generally isomeric mixtures having 1 to 3 chloromethyl groups, the chloromethyl groups preferably being located e.g. in the o- and p-positions of the two benzene rings. Accordingly, the corresponding sulfonated condensation products are also generally in the form of mixtures, especially of monosubstituted to trisubstituted biphenyl or diphenyl ether products. The relative proportions of the isomers vary according to the starting materials and the selected reaction conditions in the preparation of the condensation products. If n is equal to 1, p-isomers are obtained in proportions of e.g. 30 to 90% and o-isomers in proportions of e.g. 70 to 10%. If n is equal to 2, p,p'-, o,o'- or o,p'-compounds, for example, are obtained.

These sulfonated condensation products and their preparation are described in German Offenlegungsschrift 23 53 691. Further details can be found in this Offenlegungsschrift.

Examples of the emulsifiers used are ethoxylated waxy or fatty alcohols which may be wholly or partly esterified with fatty acids, polyalcohols or, preferably, alkoxylated polyalcohols (e.g. glycol, diglycol, alkylene or dialkylene glycols, sorbitan, sorbitol, mannitol, xylitol, pentaerythritol, diglycerol, glycerol and glycerylsorbitol) which are wholly or partly esterified with fatty acids, ethoxylated sugar derivatives (e.g. sucrose or glucose derivatives) which may be esterified with fatty acids, phosphoric acid esters (monoesters, diesters and triesters and mixtures thereof) of ethoxylated or non-ethoxylated waxy or fatty alcohols, and fatty acid monoalkanolamides or dialkanolamides. Suitable starting materials for the emulsifiers used according to the invention are e.g. stearyl, oleyl, cetyl or lanolyl alcohol, wool fatty alcohol or wool waxy alcohol in the case of the waxy or fatty alcohols, and e.g. myristic, palmitic, stearic, isostearic, oleic, linoleic, linolenic or lanolic acid in the case of the fatty acids. It is also possible to use naturally occurring substances (e.g. zoosterols or phytosterols), cationic emulsifiers and hydrotropic solubilizers (e.g. polyalcohol/polyglycol ethers of polyethoxylated fatty acids), as well as adducts of fatty or waxy alcohols and about 10 to 30 mol of ethylene oxide and, if appropriate, propylene oxide.

UV absorbers can be used in addition to the light stabilizers from the class of the sterically hindered amines. It is possible to use any compounds which are known as UV absorbers and are described e.g. in KirkOthmer 23, 615–627, A. F. Strobel, ADR, 50 (1961) 583–588 and 51 (1962) 99–104, and R. Gächter and H. Müller, Taschenbuch der Kunststoff-Additive (Pocket Edition of Plastics Additives), Carl Hanser Verlag, Munich, p. 101–198 (1983), and in U.S. Pat. No. 4,511,596.

Preferably, however, water-solubilized UV absorbers, described e.g. in WO 86/03528, WO 88/00942 and U.S. Pat. No. 4,770,667, are suitable.

The following compounds, for example, can be used:

a) 2-Hydroxybenzophenones of formula (VII)

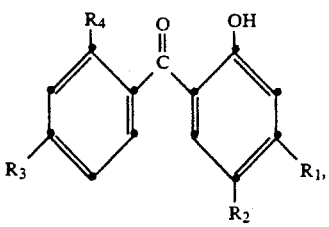

wherein R₁ is hydrogen, hydroxyl, $C_1-C_{14}$ alkoxy or phenoxy, R₂ is hydrogen, halogeno, $C_1-C_4$ alkyl or sulfo, R₃ is hydrogen, hydroxyl or $C_1-C_4$ alkoxy and R₄ is hydrogen, hydroxyl or carboxyl, e.g. the 4-hydroxy, 4-methoxy, 4-octyloxy, 4-decyloxy, 4-dodecyloxy, 4-methoxy-2′-carboxy, 4,2′,4′-trihydroxy, 4,4′-dimethoxy-2′-hydroxy, 4-methoxy-5-sulfo, 2′-hydroxy-4,4′-dimethoxy-5-sulfo, 4-benzyloxy and 5-chloro derivatives.

b) 2-(2′-Hydroxyphenyl)benzotriazoles of formula (VIII)

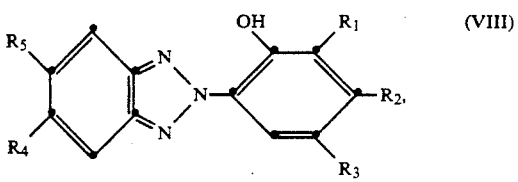

wherein R₁ is hydrogen, $C_1-C_{12}$ alkyl, chloro, $C_5-C_6$ cycloalkyl, $C_7-C_9$ phenylalkyl or sulfo, R₂ is hydrogen, $C_1-C_4$ alkyl, $C_1-C_4$ alkoxy, chloro, hydroxyl or sulfo, R₃ is $C_1-C_{12}$ alkyl, $C_1-C_4$ alkoxy, phenyl, ($C_1-C_8$ alkyl)-phenyl, $C_5-C_6$ cycloalkyl, $C_2-C_9$ alkoxycarbonyl, chloro, carboxyethyl, $C_7-C_9$ phenylalkyl or sulfo, R₄ is hydrogen, chloro, $C_1-C_4$ alkyl, $C_1-C_4$ alkoxy, $C_2-C_9$ alkoxycarbonyl, carboxyl or sulfo and R₅ is hydrogen or chloro, e.g. the 5′-methyl, 3′,5′-di-tert-butyl, 5′-tert-butyl, 5′-(1,1,3,3-tetramethylbutyl), 5-chloro-3′,5′-di-tert-butyl, 5-chloro-3′-tert-butyl-5′-methyl, 3′-sec-butyl-5′-tert-butyl, 4′-octyloxy, 3′,5′-di-tert-amyl and 3′,5′-bis-(α,α-dimethylbenzyl) derivatives.

c) 2-(2′-Hydroxyphenyl)-s-triazines of formula (IX)

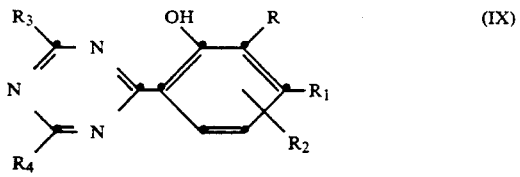

wherein R is hydrogen, halogeno, $C_1-C_4$ alkyl or sulfo, R₁ is hydrogen, $C_1-C_4$ alkyl, $C_1-C_4$ alkoxy or hydroxyl, R₂ is hydrogen or sulfo and R₃ and R₄ independently of the other are $C_1-C_4$ alkyl, $C_1-C_4$ alkoxy, $C_5-C_6$ cycloalkyl, phenyl or phenyl substituted by $C_1-C_4$ alkyl and hydroxyl, it being possible for the sulfo groups to be in the free form or in the form of salts, e.g. in the form of alkali metal, alkaline earth metal, ammonium or amine salts. Examples of compounds of formula (IX) are 2-(2′,4′-di-hydroxyphenyl)-4,6-diphenyl-s-triazine, 2-(2′-hydroxy-4′-methoxyphenyl)-4,6-diphenyl-s-triazine, 2-(2′-hydroxy-4′-methoxyphenyl)-4,6-diphenyl-s-triazine, 2-(2′-hydroxy-5′-methylphenyl)-4,6-diphenyl-s-triazine, 2,4-bis(2′-hydroxy-3′-methylphenyl)-6-ethyl-s-triazine, 2,4-bis(2′-hydroxyphenyl)-6-methoxy-s-triazine, 2,4-bis-cyclohexyl-6-(2′-hydroxy-4′-methoxyphenyl)-s-triazine, 2-(2′-hydroxy-4′-methoxy-5′-sulfophenyl)-4,6-diphenyl-s-triazine or 2-(2′-hydroxy-4′-methoxy-5′-sulfophenyl)-4-(3′-sulfo-4′-methylphenyl)-6-(4′-tolyl)-s-triazine.

d) s-Triazine compounds of the formula

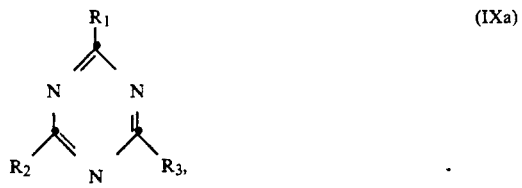

wherein at least one of the substituents R₁, R₂ and R₃ is a radical of the formula

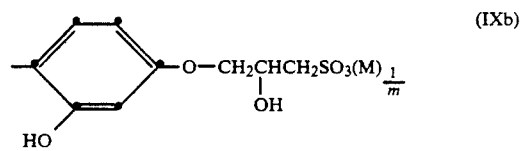

wherein M is sodium, potassium, calcium, magnesium, ammonium or tetra($C_1-C_4$ alkyl)ammonium and m is 1 or 2, and the remaining substituent or the remaining substituents independently of the other are $C_1-C_{12}$ alkyl, phenyl or $C_1-C_{12}$ alkyl or phenyl bonded to the triazinyl radical via oxygen, sulfur, imino or $C_1-C_{11}$ alkylimino, e.g. the potassium salt of the compound of formula (IXa) wherein R₁ is phenyl and R₂ and R₃ are each the radical of formula (IXb), or the sodium salt of the compound of formula (IXa) wherein R₁ is p-chlorophenyl and R₂ and R₃ are each the radical of formula (IXb). Further compounds are described in European patent application 165608.

The compounds of formulae (VII) and (VIII) can be prepared by processes known per se, as described e.g. in U.S. Pat. No. 3,403,183 or 4,127,586.

The compounds of formula (IX) can be prepared in a manner known per se, e.g. by the processes described in Helv. 55, 1566–1595 (1972).

The dispersed or emulsified light stabilizer can be applied batchwise, before or during dyeing, by an exhaustion process with liquor ratios of 1:5 to 1:500, preferably 1:10 to 1:50. The light stabilizer is conveniently added direct to the dyebath.

However, the light stabilizers can also be applied continuously by means of short-liquor application systems or hot application systems.

The amount of light stabilizer added depends on the substrate and the desired stabilization. In general, 0.01 to 10% by weight, preferably 0.05 to 5% by weight, based on the substrate, is used.

The light stabilizers which can be used according to the invention may be employed as such or in the form of their water-soluble salts. Suitable salts are those of organic acids such as carboxylic acids having 1 to 12 carbon atoms, e.g. formic, acetic, propionic, butyric, valeric, caproic and caprylic acids, or those of inorganic, polybasic oxygen-containing acids, e.g. sulfuric acid or orthophosphonic acid. The formic or acetic acid salts are preferred. Salts of compounds of formula (II) wherein $R^1$ is hydrogen or $C_1-C_{12}$ alkyl are especially preferred.

Preferred oligomeric compounds are those with a low molecular weight (<700).

The present invention further relates to a composition for carrying out the process of the invention, which comprises
1) 20 to 80% by weight of a light stabilizer from the class of the sterically hindered amines,
2) 0 to 40% by weight of a dispersant,
3) 0 to 25% by weight of an emulsifier and
4) ad 100% by weight of water and/or an organic solvent, only one of components 2 and 3 being used in each case.

The composition of the invention conveniently comprises
1) 20 to 60% by weight of a light stabilizer,
2) 0 to 30% by weight of a dispersant,
3) 0 to 15% by weight of an emulsifier and
4) ad 100% by weight of water and/or an organic solvent,
only one of components 2 and 3 being used in each case.

Polyamide fibre material is understood as meaning synthetic polyamide having an affinity for acid or basic dyes, e.g. polyamide 6, polyamide 66 or polyamide 12. In addition to pure polyamide fibres, it is also possible to use, in particular, blends of different polyamide fibres and of polyurethane and polyamide, e.g. tricot material consisting of polyamide/polyurethane in a blend ratio of 70:30. Fibre blends of polypropylene and polyamide are also suitable. In principle, the pure or blended polyamide material can have various forms of presentation, e.g. fibre, yarn, woven fabric or knitted fabric.

The present process is particularly advantageous for the treatment of polyamide material in blends with polyurethane or polypropylene, which is exposed to light and heat and is used e.g. as motor vehicle upholstery material, carpeting or swimwear material.

Dyeing is carried out in conventional manner, e.g. with metal complex dyes or else with anthraquinone dyes or azo dyes. The known types of metal complex dyes are used, especially the 1:2 chromium complexes or 1:2 cobalt complexes of monoazo, disazo or azomethine dyes, a large number of which are described in the literature. In addition to these, other classes of dyes are of course also suitable, e.g. disperse dyes or else vat dyes.

The following Preparatory Procedures and Examples will serve to illustrate the invention. Parts and percentages are by weight. The percentages relating to the ingredients of the individual treatment baths or dyebaths are based on the fibre material, unless indicated otherwise.

EXAMPLE 1

Two 20 g samples of a polyamide looped carpet consisting of one third each of so-called RDB fibres (dyeing affinity: R=regular, D=deep, B=basic) are prepared.

This material is dyed in an open dyeing machine, e.g. an ⓇAHIBA, with a liquor ratio of 1:30. 2 liquors are prepared for this purpose, each of which contains

| | |
|---|---|
| 1% of an alkylamino polyglycol ether (dyeing assistant) | |
| 0.5 g/l of sodium acetate | pH 5,5 |
| 0.5 ml/g of acetic acid (80%) | |

Liquor 1 contains no further ingredients other than the dyes added later. Liquor 2, on the other hand, additionally contains 1.5% of an emulsion consisting of 75% of the compound of formula (101)

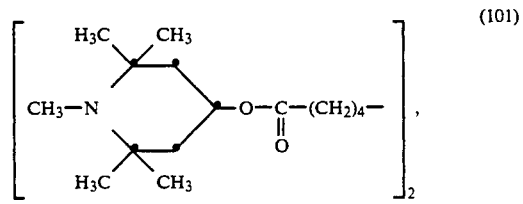

10% of an adduct of 1 mol of nonylphenol and 9–10 mol of ethylene oxide, and 15% of a $C_{10}$–$C_{13}$ alkylbenzene. The two carpet samples are then treated for 20 minutes in these liquors, heated to 45° C. After the samples have been removed from the liquors, the following dyes (dissolved in water) are added to the liquor in identical amounts in each case:

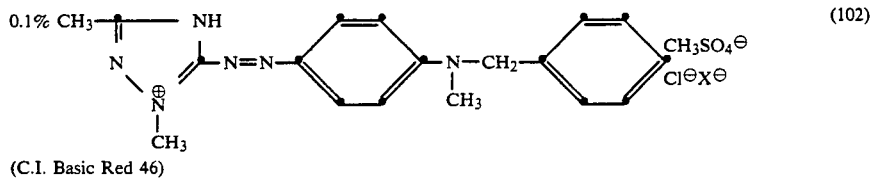

(C.I. Basic Red 46)

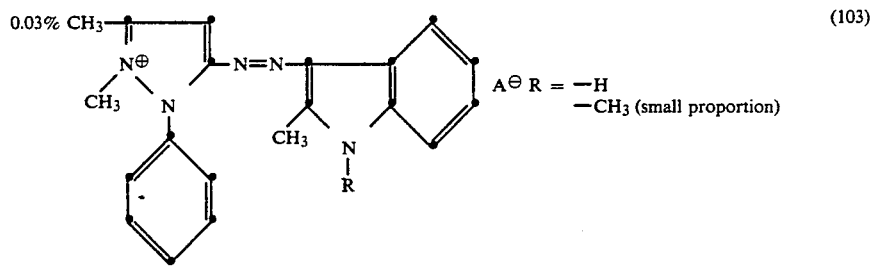

(C.I. Basic Yellow 45)

The two samples are put back into the liquor and treated for a further 10 minutes at 40° C., the liquor is heated to 90° C. over a period of 30 minutes and the samples are dyed at this temperature for a further 30 minutes. Finally, the liquor is cooled to 70° C. and the samples are rinsed with cold water, centrifuged and dried at 80° C.

Both dyeings are tested for light fastness according to SN-ISO 105-B02 (=Xenon) and DIN 75.202 (=Fakra).

The addition of compound 101 markedly improves the light fastness properties of the basic-dyed PA and markedly inhibits the yellowing tendency.

EXAMPLE 2

The procedure is as described in Example 1, except that the compound of formula 101 is replaced with a 20% dispersion of the compound of formula (104), prepared by sand grinding with the sodium salt of the condensation product of formaldehyde and naphthalenesulfonate in proportions of 1:1.

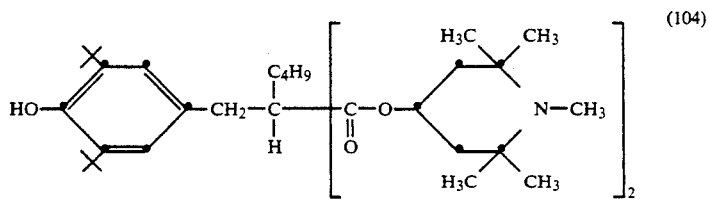

If these dyeings are tested for light fastness properties, a marked improvement in the fastness to hot light according to Fakra is achieved with this product as well.

EXAMPLE 3

Two 10 g samples of a nylon carpet yarn are treated in an open dyeing machine at 45° C. for 20 minutes, with a liquor ratio of
1:30, in liquors containing
0.25% of monosodium phosphate and
1.75% of disodium phosphate.
The liquor for dyeing No. 2 additionally contains 1.5% of the emulsion of the compound of formula (101) (see Example 1).

After the pretreatment, 0.12% of the dye of the formula

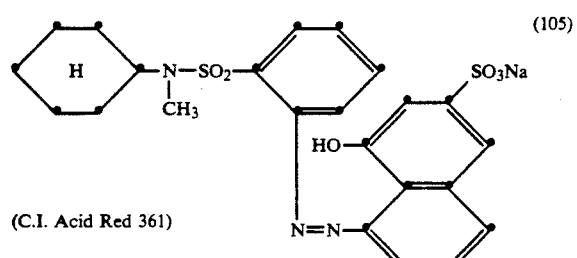

(C.I. Acid Red 361)

dissolved in water, is added.

Both yarn samples are tested for their light fastness properties [according to SN-ISO 105-B02 (=Xenon) and DIN 75.202 (=Fakra)]. To test the photochemical degradation, the yarns are singly wound on to cardboard, exposed for 144 hours according to DIN 75.202 and then tested for tensile strength and elongation according to SNV 197.461. In another test, both dyeings are subjected to heat at 130° C. for 50 h. Table I contains the test results:

TABLE I

| DYEING | *LIGHT FASTNESS PROPERTIES | | TENSILE STRENGTH/ ELONGATION | HEAT TEST |
|---|---|---|---|---|
| | XENON | FAKRA 72 h | after 144 h Fakra | |
| 1 | 6 | <4 | 5,3 \| 15,1% | Yellowing and dye |
| 2 | 6-7 | 6 | 70,5 \| 74,2% | destruction much sooner (~25 h) in the case of dyeing 1 than in the case of dyeing 2 |

*according to blue scale
**unexposed dyeing as standard

It can be seen that light fastness properties and fibre stability are markedly improved by treatment with the compound of formula (101) and also that yellowing caused by heat is delayed.

EXAMPLES 4-6

Four 10 g samples of a polyamide 6 knitted fabric are dyed in an open dyeing machine, with a liquor ratio of 1:25, from baths which each contain
0.25 g/l of monosodium phosphate,
1.75 g/l of disodium phosphate and
0.01% of the 1:2 cobalt complex dye of formula (106)

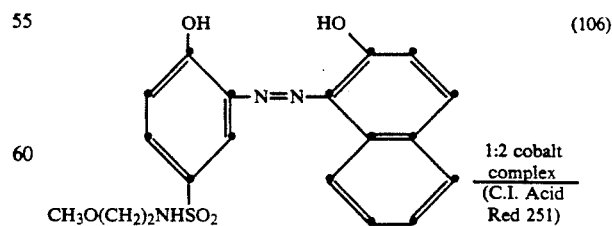

1:2 cobalt complex (C.I. Acid Red 251)

Dyebath 1 contains no additional ingredients and dyebaths 2-4 each contain 1% of compounds 107-109 as fine * dispersions.
* (=produced by sand grinding with the condensation product of naphthalenesulfonic acid and formaldehyde: weight ratio 1:1)

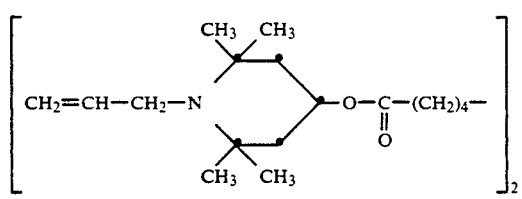
(107)

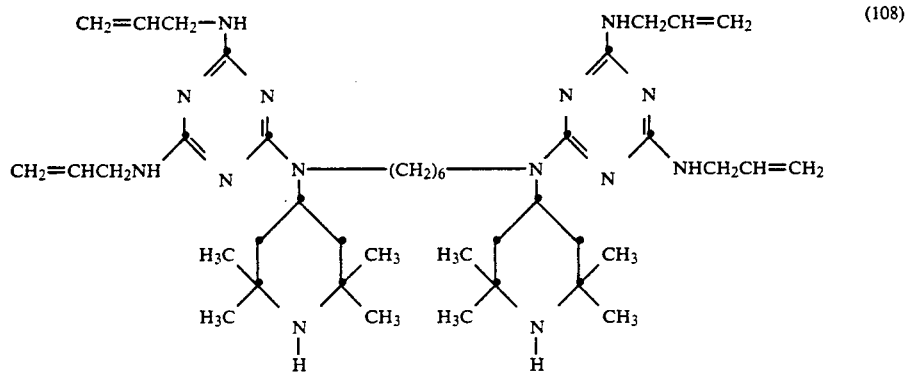
(108)

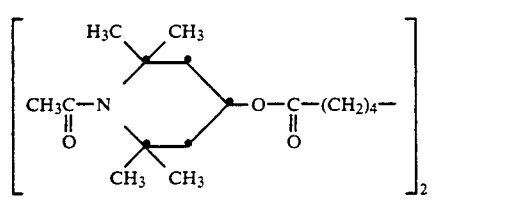
(109)

The fabric samples are put into the dyebath at 40° C., the liquor is heated to 95° C. over a period of 30 minutes and the samples are dyed at this temperature for 30 minutes. The dyeings are rinsed, centrifuged and dried. Determination of the light fastness properties according to DIN 75.202 (=Fakra) gives the results collated in Table II:

TABLE II

| DYE-ING | LIGHT FASTNESS PROPERTIES according to FAKRA* | | MECHANICAL STRENGTH after EXPOSURE |
|---|---|---|---|
| | 144 h | 288 h | |
| 1 | 1 H | 1 H | after 144/288 h:low/zero |
| 2 | 3 H | 2 H | } Samples are still intact |
| 3 | −3-4 H | 2+ H | |
| 4 | −3 H | 2 H | |

*evaluation according to grey scale

EXAMPLE 7

Four 10 g samples of a ®Nylon/®Lycra tricot (70/30) are treated in an open dyeing machine (e.g. ®AHIBA), with a liquor ratio of 1:25, in liquors containing the following ingredients:

Liquor a: 2% of an alkylamino polyglycol ether; 1% of acetic acid (80%)

Liquor b: as liquor a with the addition of 0.75% of the compound of formula (110)

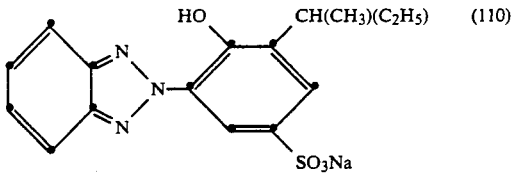
(110)

Liquor c: as liquor a with the addition of 1.5% of the emulsion of compound (101)

Liquor d: as liquor a with the addition of 0.75% of the compound of formula (110); 1.50% of the emulsion of compound (101)

The tricot samples are treated for 20 minutes in liquors a) to d), heated to 50° C. 0.25% of the dye of formula (111)

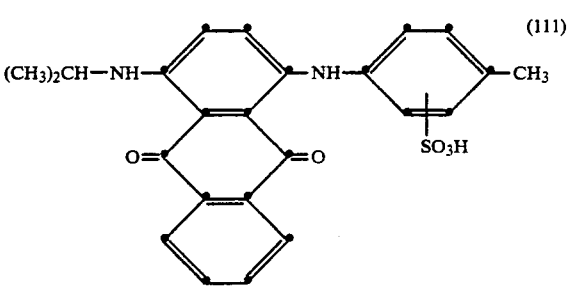
(111)

(Cl. Acid Blue 258)

in dissolved form, is then added to each of liquors a) to d). After a 10-minute treatment at 50° C., the dyebath is heated to 95° C. over a period of 30 minutes. The samples are dyed at this temperature for 30 minutes and the liquor is cooled to 70° C. The samples are then rinsed with cold water and dried at 60° C.

The light fastness properties of the dyeings are tested according to SN-ISO 105 B02 (Xenon) and according to DIN 75.202 (FAKRA). Tensile strength and elongation are also tested according to SNV 198.461 after exposure for 72 h according to DIN 75.202. The results are collated in Table III:

TABLE III

| DYEING | LIGHT FAST-NESS PROPERTIES | | *TENSILE STRENGTH/ ELONGATION in % |
|---|---|---|---|
| | Xenon | Fakra | after EXPOSURE |
| Liquor a | 6-7 | 4 | 36\|55% |
| Liquor b | 7 | 6+ | 59\|67% |
| Liquor c | 6-7 | -5 | 69\|76% |
| Liquor d | 7+ | 6-7 | 74\|87% |

*based on dyeings before exposure

What is claimed is:

1. A process for the photochemical and thermal stabilization of polyamide fibers having an affinity for acid and basic dyes, and of blends of said fibers with one another and with polyurethane or polypropylene fibers, which comprises treating the fibers in the absence of copper complex compounds with an aqueous liquor comprising from 20 to 80 percent by weight of a hindered amine light stabilizer, 0 to 40 percent by weight of a dispersant, and 0 to 25 percent by weight of an emulsifier.

2. A process according to claim 1, wherein the light stabilizer used is a sterically hindered amine whose molecule contains at least one group of formula I

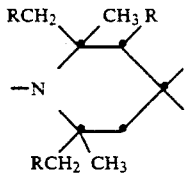

wherein R is hydrogen or methyl.

3. A process according to claim 1, wherein the light stabilizer used is a sterically hindered amine of formula II

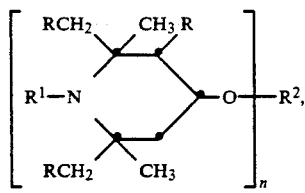

or water-soluble salts thereof, wherein n is a number from 1 to 4, R is hydrogen or methyl, $R^1$ is hydrogen, hydroxyl, $C_1$-$C_{12}$ alkyl, $C_3$-$C_8$ alkenyl, $C_3$-$C_8$ alkynyl, $C_7$-$C_{12}$ aralkyl, $C_1$-$C_8$ alkanoyl, $C_3$-$C_5$ alkenoyl, glycidyl, —O—$C_1$—$C_{12}$ alkyl, —O—$C_1$—$C_8$ alkanoyl or a group —$CH_2CH(OH)$—Z, wherein Z is hydrogen, methyl or phenyl, $C_1$-$C_4$ alkyl, allyl, benzyl, acetyl or acryloyl, and $R^2$, when n is 1, is hydrogen, $C_1$-$C_{18}$ alkyl group, $C_1$-$C_{18}$ alkyl group which contains one or more oxygen atoms, cyanoethyl, benzyl, glycidyl, a monovalent radical of an aliphatic, cycloaliphatic, araliphatic, unsaturated or aromatic carboxylic acid, carbamic acid or phosphorus-containing acid, or a monovalent silyl radical, $R^2$ when n is 2 is $C_1$-$C_{12}$ alkylene, $C_4$-$C_{12}$ alkenylene, xylylene, a divalent radical of an aliphatic, cycloaliphatic, araliphatic or aromatic dicarboxylic acid, dicarbamic acid or phosphorus-containing acid, or a divalent silyl radical, $R^2$ when n is 3 is a trivalent radical of an aliphatic, cycloaliphatic or aromatic tricarboxylic acid, aromatic tricarbamic acid or phosphorus-containing acid, or a trivalent silyl radical, and $R^2$ when n is 4 is a tetravalent radical of an aliphatic, cycloaliphatic or aromatic tetracarboxylic acid.

4. A process according to claim 1, wherein the hindered amine light stabilizer is a sterically hindered amine of formula (III)

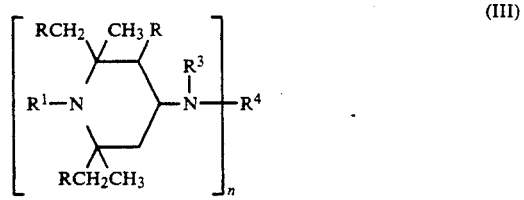

wherein n is the number 1 or 2, R is hydrogen or methyl, $R^1$ is hydrogen, hydroxyl, $C_1$-$C_{12}$ alkyl, $C_3$-$C_8$ alkenyl, $C_3$-$C_8$ alkynyl, $C_7$-$C_{12}$ aralkyl, $C_1$-$C_8$ alkanoyl, $C_3$-$C_5$ alkenoyl, glycidyl, —O—$C_1$—$C_{12}$ alkyl, —O—$C_1$—$C_8$ alkanoyl or a group —$CH_2CH(OH)$—Z, wherein Z is hydrogen, methyl or phenyl, $R_3$ is hydrogen, $C_1$-$C_{12}$ alkyl, $C_2$-$C_5$ hydroxyalkyl, $C_5$-$C_7$ cycloalkyl, $C_7$-$C_8$ aralkyl, $C_2$-$C_{18}$ alkanoyl, $C_3$-$C_5$ alkenoyl or benzoyl and $R^4$ when n is 1 is hydrogen, $C_1$-$C_{18}$ alkyl, $C_3$-$C_8$ alkenyl, $C_5$-$C_7$ cycloalkyl, $C_1$-$C_4$ alkyl substituted by a hydroxyl, cyano, alkoxycarbonyl or carbamide group, glycidyl, —$CH_2$—CH(OH)—Z or —CONH—Z, wherein Z is hydrogen, methyl or phenyl, $R^4$ when n is 2 is $C_2$-$C_{12}$ alkylene, $C_6$-$C_{12}$ arylene, xylylene, —$CH_2$—CH(OH)—$CH_2$— or —$CH_2$—CH(OH)—$CH_2$—O—D—O—, wherein D is $C_2$-$C_{10}$ alkylene, $C_6$-$C_{15}$ arylene or $C_6$-$C_{12}$ cycloalkylene, or, with the proviso that $R^3$ is not alkanoyl, alkenoyl or benzoyl, or $R^4$ is divalent radical of an aliphatic, cycloaliphatic or aromatic dicarboxylic acid or dicarbamic acid, or —CO—, or $R^3$ and $R^4$, when n is 1, are together the divalent radical of an aliphatic, cycloaliphatic or aromatic 1,2- or 1,3-dicarboxylic acid.

5. A process according to claim 1, wherein the hindered amine light stabilizer used is a compound of general formula (IV)

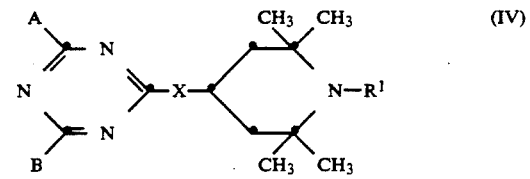

wherein $R^1$ is hydrogen, oxyl oxygen, $C_1$-$C_{12}$ alkyl, $C_3$-$C_7$ alkenyl, $C_7$-$C_{11}$ phenylalkyl, cyanomethyl, $C_2$-$C_{18}$ alkanoyl, $C_3$-$C_{18}$ alkenoyl, a group —CON($R^2$)($R^3$) or a group —$CH_2$—CH($R^4$)—OH, wherein $R^2$ is $C_1$-$C_{12}$ alkyl, allyl, cyclohexyl, benzyl, phenyl or $C_7$-$C_{12}$ alkylphenyl and $R^3$ is hydrogen, $C_1$-$C_{12}$ alkyl, allyl or benzyl, or $R^2$ and $R^3$ form a 5- or 6-membered heterocyclic ring together with the N atom to which they are bonded, and $R^4$ is hydrogen, $C_1$-$C_{12}$ alkyl, phenyl, $C_2$-$C_{13}$ alkoxymethyl or phenoxymethyl, X is a divalent group of the formula —O—, —N(R$^5$)—, —N-H—(CH$_2$)$_2$—O—, —NH—(CH$_2$)$_3$—O— or —N(R$^5$)—R$^7$—N(R$^6$)—, wherein R$^5$ is hydrogen, C$_1$-C$_{12}$ alkyl, C$_3$-C$_7$ alkenyl, cyclohexyl, C$_3$-C$_{12}$ alkoxyalkyl, C$_5$-C$_{12}$ alkenoxyalkyl, C$_4$-C$_{12}$ dialkylaminoalkyl, a group —CH$_2$—CH(R$^4$)—OH, benzyl or a group of the formula

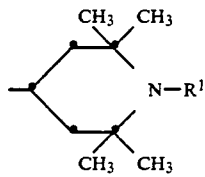

or of the formula

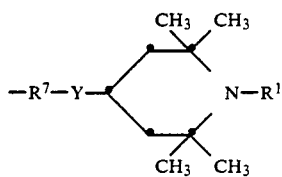

R$^6$ is hydrogen, C$_1$-C$_{12}$ alkyl, C$_3$-C$_7$ alkenyl, cyclohexyl, a group —CH$_2$—CH(R$^4$)—OH or a group of the formula

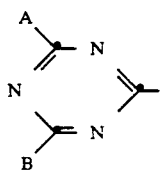

R$^7$ is C$_2$-C$_{12}$ alkylene which can be interrupted by 1, 2 or 3 of the groups —O— or —N(R$^6$)—, C$_6$-C$_{14}$ cycloalkylene or cycloalkylenedialkylene and Y is a divalent group of the formula —O— or —N(R$^6$)—, and A and B independently of the other are a group of the formula R$^8$O— or (R$^9$)(R$^{10}$)N—, wherein R$^8$ is C$_1$-C$_{12}$ alkyl, C$_3$-C$_7$ alkenyl, cyclohexyl, benzyl, phenyl or C$_7$-C$_{12}$ alkylphenyl, R$^9$ is C$_1$-C$_{12}$ alkyl, C$_3$-C$_7$ alkenyl, C$_5$-C$_8$ cycloalkyl, C$_3$-C$_{12}$ alkoxyalkyl, C$_5$-C$_{12}$ alkenoxyalkyl, a group —CH$_2$—CH(R$^4$)—OH, phenyl, C$_7$-C$_{12}$ alkylphenyl or C$_7$-C$_{11}$ phenylalkyl and R$^{10}$ is hydrogen, C$_1$-C$_{12}$ alkyl, C$_3$-C$_7$ alkenyl, C$_5$-C$_8$ cycloalkyl, C$_3$-C$_{12}$ alkoxyalkyl, C$_5$-C$_{12}$ alkenoxyalkyl, a group —CH$_2$—CH(R$^4$)—OH or C$_7$-C$_{11}$ phenylalkyl, or R$^9$ and R$^{10}$ form a 5- or 6-membered heterocyclic ring together with the N atom to which they are bonded.

6. A process according to claim 5, wherein A and B are a group of the formula R$^{15}$O— or (R$^{15}$)(R$^{10}$)N— and R$^{15}$ is allyl.

7. A process according to claim 1, wherein a water-soluble ultra violet (UV) absorber is additionally used.

8. A process according to claim 7, wherein the UV absorber used is a 2-hydroxybenzophenone of the formula

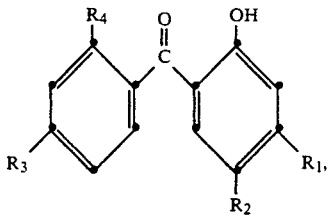

wherein R$_1$ is hydrogen, hydroxyl, C$_1$-C$_{14}$ alkoxy or phenoxy, R$_2$ is hydrogen, halogeno, C$_1$-C$_4$ alkyl or sulfo, R$_3$ is hydrogen, hydroxyl or C$_1$-C$_4$ alkoxy and R$_4$ is hydrogen, hydroxyl or carboxyl.

9. A process according to claim 7, wherein the UV absorber used is a 2-(2'-hydroxyphenyl)benzotriazole of the formula

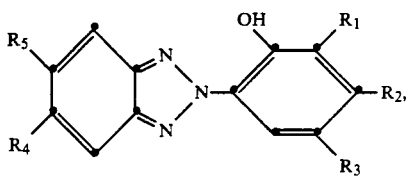

wherein R$_1$ is hydrogen, C$_1$-C$_{12}$ alkyl, chloro, C$_5$-C$_6$ cycloalkyl, C$_7$-C$_9$ phenylalkyl or sulfo, R$_2$ is hydrogen, C$_1$-C$_4$ alkyl, C$_1$-C$_4$ alkoxy, chloro or hydroxyl, R$_3$ is C$_1$-C$_{12}$ alkyl, C$_1$-C$_4$ alkoxy, phenyl, (C$_1$-C$_8$ alkyl)phenyl, C$_5$-C$_6$ cycloalkyl, C$_2$-C$_9$ alkoxycarbonyl, chloro, carboxyethyl, C$_7$-C$_9$ phenylalkyl or sulfo, R$_4$ is hydrogen, chloro, C$_1$-C$_4$ alkyl, C$_1$-C$_4$ alkoxy, C$_2$-C$_9$ alkoxycarbonyl, carboxyl or sulfo and R$_5$ is hydrogen or chloro.

10. A process according to claim 7, wherein the UV absorber used is a 2-(2'-hydroxyphenyl)-s-triazine of the formula

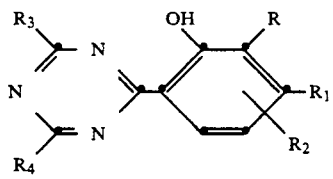

wherein R is hydrogen, halogeno, C$_1$-C$_4$ alkyl or sulfo, R$_1$ is hydrogen, C$_1$-C$_4$ alkyl, C$_1$-C$_4$ alkoxy or hydroxyl, R$_2$ is hydrogen or sulfo and R$_3$ and R$_4$ independently of the other are C$_1$-C$_4$ alkyl, C$_1$-C$_4$ alkoxy, C$_5$-C$_6$ cycloalkyl, phenyl or phenyl substituted by C$_1$-C$_4$ alkyl and hydroxyl.

11. A process according to claim 7, wherein the UV absorber used is an s-triazine compound of the formula

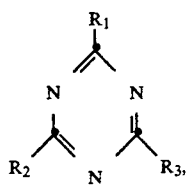

wherein at least one of the substituents R$_1$, R$_2$ and R$_3$ is a radical of the formula

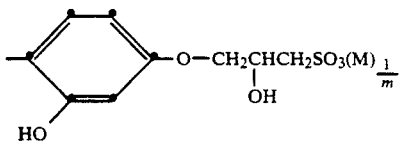

wherein M is sodium, potassium, calcium, magnesium, ammonium or tetra($C_1$-$C_4$ alkyl)ammonium and m is 1 or 2, and the remaining substituent or the remaining substituents independently of the other are $C_1$-$C_{12}$ alkyl, phenyl or $C_1$-$C_{12}$ alkyl or phenyl bonded to the triazinyl radical via oxygen, sulfur, imino or $C_1$-$C_{11}$ alkylimino.

12. A process according to claim 1, wherein the polyamide fibre is treated with the light stabilizer before or during dyeing.

13. A process according to claim 12, wherein the fibre is treated with the light stabilizer during dyeing.

14. A process according to claim 1, wherein the treatment is carried out batchwise by an exhaustion process, or continuously.

15. A fibre material treated by a process according to claim 1.

16. A process according to claim 3 wherein n is 1 or 2 and $R^1$ is hydrogen.

17. A process according to claim 3 wherein n is 1 and $R^2$ is a radical of an aliphatic carboxylic acid having 2 to 18 C atoms, of a cycloaliphatic carboxylic acid having 7 to 15 C atoms, of an α,β-unsaturated carboxylic acid having 3 to 5 C atoms or of an aromatic carboxylic acid having 7 to 15 C atoms.

18. A process according to claim 3 wherein n is 2 and $R^2$ is a radical of an aliphatic dicarboxylic acid having 2 to 36 C atoms, of a cycloaliphatic or aromatic dicarboxylic acid having 8 to 14 C atoms or of a cycloaliphatic or aromatic dicarbamic acid having 8 to 14 C atoms.

19. A process of claim 3 wherein n is 1 or 2, $R^1$ is hydrogen and, when n is 1, $R^2$ is a radical of an aliphatic carboxylic acid having 2 to 18 C atoms, of a cycloaliphatic carboxylic acid having 7 to 15 C atoms, of an α,β-unsaturated carboxylic acid having 3 to 5 C atoms or of an aromatic carboxylic acid having 7 to 15 C atoms or, when n is 2, $R^2$ is radical of an aliphatic dicarboxylic acid having 2 to 36 C atoms, of a cycloaliphatic or aromatic dicarboxylic acid having 8 to 14 C atoms or of a cycloaliphatic or aromatic dicarbamic acid having 8 to 14 C atoms.

* * * * *